US 10,729,865 B2

(12) United States Patent
Bahns et al.

(10) Patent No.: US 10,729,865 B2
(45) Date of Patent: Aug. 4, 2020

(54) DEVICE FOR THE PRESSURE-SUPPORTED OR PRESSURE-CONTROLLED VENTILATION OF A PATIENT WITH REDUCED SPONTANEOUS BREATHING (71) Applicant: Drägerwerk AG & Co. KGaA, Lübeck (DE)

(72) Inventors: Ernst Bahns, Bad Schwartau (DE); Marcus Eger, Lübeck (DE)

(73) Assignee: DRÄGERWERK AG & CO. KGAA, Lübeck (DE)

(*) Notice: Subject to any disclaimer, the term of this patent is extended or adjusted under 35 U.S.C. 154(b) by 171 days.

(21) Appl. No.: 15/342,460

(22) Filed: Nov. 3, 2016

(65) Prior Publication Data
US 2017/0119984 A1    May 4, 2017

(30) Foreign Application Priority Data
Nov. 3, 2015  (DE) .................. 10 2015 014 106

(51) Int. Cl.
*A61B 5/00* (2006.01)
*A61M 16/00* (2006.01)
(Continued)

(52) U.S. Cl.
CPC ..... *A61M 16/0057* (2013.01); *A61B 5/04012* (2013.01); *A61B 5/0488* (2013.01);
(Continued)

(58) Field of Classification Search
CPC ............ A61M 16/0057; A61M 16/026; A61M 2016/0036; A61M 2016/0027;
(Continued)

(56) References Cited

U.S. PATENT DOCUMENTS 5,800,470 A * 9/1998 Stein .................. A61N 1/36514
607/20
5,820,560 A * 10/1998 Sinderby ............ A61B 5/04884
600/546
(Continued)

FOREIGN PATENT DOCUMENTS

DE  10 2007 062 214 B3  8/2009
DE  10 2010 055 253 A1  6/2012
DE  10 2012 003 509 A1  8/2013

OTHER PUBLICATIONS

Spiet, P. M. et al.; Effects of Different Levels of Pressure Support Variability in Experimental Lung Injury; Anesthesiology 2009; 110: 342-350.
(Continued)

*Primary Examiner* — Sean P Dougherty
*Assistant Examiner* — David Joseph Fernandez-Fidalgo
(74) *Attorney, Agent, or Firm* — McGlew and Tuttle, P.C.

(57) ABSTRACT

A device, for the pressure-supported or pressure-controlled ventilation of a patient with reduced spontaneous breathing, has a ventilator unit to supply a breathing air flow composed of cyclical ventilation strokes and a control unit generating a control signal to set a pressure and/or a volume flow of the breathing air flow. An EMG unit generates an EMG signal, which may be used as a basis for generating the control signal as a function of a breath of the patient. A unit for analyzing an EMG signal is provided, which analyzes at least one EMG signal recorded during an already concluded breath of the patient. The control unit is configured such that the ventilator unit control signal can be generated, at least at times, by taking into account the analysis of the EMG signal recorded during an already concluded breath of the patient.

14 Claims, 3 Drawing Sheets (51) Int. Cl.
*A61B 5/04* (2006.01)
*A61B 5/0488* (2006.01)
*A61B 5/08* (2006.01)

(52) U.S. Cl.
CPC ............. *A61B 5/08* (2013.01); *A61M 16/026* (2017.08); *A61M 2016/0027* (2013.01); *A61M 2016/0036* (2013.01); *A61M 2205/3334* (2013.01); *A61M 2230/60* (2013.01)

(58) Field of Classification Search
CPC ...... A61M 2205/3334; A61M 2230/60; A61M 2230/08; A61M 2230/005; A61B 5/0488; A61B 5/04012; A61B 5/08; A61B 5/7203; A61B 5/7221
See application file for complete search history.

(56) References Cited

U.S. PATENT DOCUMENTS

| | | | | |
|---|---|---|---|---|
| 6,588,423 | B1* | 7/2003 | Sinderby | A61B 5/04884 128/200.24 |
| 6,962,155 | B1* | 11/2005 | Sinderby | A61M 16/026 128/204.18 |
| 2003/0066528 | A1* | 4/2003 | Hill | A61M 16/026 128/204.18 |
| 2012/0015225 | A1 | 6/2012 | Eger et al. | |
| 2012/0152250 | A1 | 6/2012 | Eger et al. | |

OTHER PUBLICATIONS

Mini-Handbuch Dräger Beatmung, Beatmungsmodi and Funktionen kurz erklärt [Dräger Mini Handbook of Ventilation; Brief Explanation of Ventilation Modes and Functions], Version 1.1; p. 6; 2014.
Wikipedia, keyword: Korrelationskoeffizient; dated Oct. 20, 2015 URL:https://de.wikipedia.org/w/index.php?title=Korrelationskoeffizienz&oldid=147208408.

* cited by examiner

EMG

Flow

FIG. 3a EMG

FIG. 3b P<sub>aw</sub>

FIG. 3c

Flow

FIG. 4a EMG

FIG. 4b P<sub>aw</sub>

FIG. 4c

Flow

DEVICE FOR THE PRESSURE-SUPPORTED OR PRESSURE-CONTROLLED VENTILATION OF A PATIENT WITH REDUCED SPONTANEOUS BREATHING

CROSS REFERENCE TO RELATED APPLICATIONS

This application claims the benefit of priority under 35 U.S.C. § 119 of German Application 10 2015 014 106.6 filed Nov. 3, 2015, the entire contents of which are incorporated herein by reference.

FIELD OF THE INVENTION

The present invention pertains to a device for the pressure-supported or pressure-controlled ventilation of a patient with reduced spontaneous breathing wherein a patient can be supplied with a breathing air flow composed of cyclical ventilation strokes, with a control device, which generates a ventilator unit control signal and transmits same to the ventilator, so that a pressure and/or a volume flow of the breathing air flow is set as a function of the ventilator unit control signal. The described device for a proportionally supporting ventilation has especially a control device, which receives signals from an EMG (electromyography) unit as a function of the patient's breathing effort, and controls the ventilator unit, which delivers a breathing gas with a pressure preset by the control unit.

BACKGROUND OF THE INVENTION

The mechanical ventilation of a patient considerably differs at times from a natural spontaneous breathing in terms of the pressures applied and the time course of the dispensing of the breathing gas. This may represent a burden for the patient. The maintenance and promotion of spontaneous breathing is therefore of increasing significance. The prior-art systems pursue, in general, two goals for promoting the spontaneous breathing, namely, to promote the spontaneous breathing breath by breath by mechanical pressure support and to train the patient to breath spontaneously, on the one hand. On the other hand, the spontaneous breathing shall be possible unhindered at any time during a pressure-controlled ventilation in order to achieve an improved ventilation or perfusion ratio thereby. It is essential in any case that the user sets machine parameters, which the patient can influence only partly if at all. In case of pressure-supported ventilation, the machine parameters set by the user are a suitable pressure value, while the inspiration time as well as a suitable pressure value are preset by the user in case of pressure-controlled ventilation.

It is often problematic, in case of pressure-supported ventilation, that, contrary to natural spontaneous breathing, tidal volumes that hardly differ from one another are obtained. A further development of conventional pressure support is variable pressure support. The value of the pressure support set by the user varies in this method [cf. Spiet, P. M. et al.; Effects of Different Levels of Pressure Support Variability in Experimental Lung Injury; Anesthesiology 2009; 110: 342-350].

Even though the tidal volumes applied vary in the course of ventilation according to this method, the corresponding change is achieved only based on a random principle, which has no recognizable relation to the physiological regulation of spontaneous breathing.

The user sets the inspiration time in patient-triggered, pressure-controlled ventilation. Methods in which the inspiration time may vary if spontaneous breathing efforts occur during the last quarter of the mechanical ventilation stroke are known in this connection (BiPAP; described in "Mini-Handbuch Dräger Beatmung, Beatmungsmodi and Funktionen kurz erklärt [Dräger Mini Handbook of Ventilation; Brief Explanation of Ventilation Modes and Functions], Version 1.1; p. 6; 2014).

The patient can trigger the switching into expiration prematurely by spontaneous breathing activity in this ventilation mode. However, the variance is achieved in this case comparatively randomly here as well, especially if the patient initiates the expiration time during the last quarter of the stroke. There is no recognizable relation to the physiological regulation of spontaneous breathing in this case, either.

Based on the above-described problems, there are efforts to improve the mechanical ventilation of a patient, and especially to carry it out more gently for the patient, with the use of EMG measuring units, which detect breathing efforts of the patient being ventilated on the basis of electromyographic signals.

A ventilation system for the non-invasive ventilation of a patient, in which the ventilation is controlled by means of EMG signals, is known in this connection from DE 10 2012 003 509 A1. It is essential for the technical solution being described that interfering ECG signal components are suppressed from the electrode signal generated by means of electrodes on the patient's thorax in order to obtain electromyographic signals (EMG signals) representing the breathing effort and to control the ventilation drive as a function of these EMG signals as accurately as possible.

Another device for automatically controlling a ventilation system is known from DE 10 2007 062 214 B3. A proportionally supporting ventilation of the lungs, of a patient being ventilated, is achieved by means of the ventilation system described. The EMG signal representing the patient's breathing activity is transformed, by means of a preset transformation rule, into a pressure signal, so that the mean deviation of the resulting pressure signal from the respiratory muscle pressure is minimized. The breathing effort pressure is determined in this case as a weighted mean.

It is, furthermore, problematic in the prior-art systems for the pressure-supported or pressure-controlled ventilation of a patient with reduced spontaneous breathing that changes in the breathing activity of the patient are taken into account for the control of the ventilation system, especially of the ventilator unit, either only insufficiently or at least with a great time delay. Another problem is often represented here by the fluctuating quality of the EMG signal, which is superimposed, on the one hand, by strong other electrical signals, for example, ECG signals, and is influenced, on the other hand, by the changing contacting of the electrodes on the thorax.

SUMMARY OF THE INVENTION

Based on the solutions known from the state of the art as well as the above-described problems, a basic object of the present invention is to perfect a device for the pressure-supported or pressure-controlled ventilation of a patient with reduced spontaneous breathing such that the ventilation can be adapted to a change in the breathing activity of the patient being ventilated as quickly as possible. Moreover, it shall be ensured that fluctuations in the quality of the EMG signal have as little an effect as possible on the generation of a control signal for the ventilator unit. Further, the system shall have a comparatively simple design and shall especially also be able to be integrated in prior-art ventilation systems, which already comprise a combination of a ventilator and an EMG system, in a comparatively simple manner.

According to the present invention a device is provided for the pressure-supported or pressure-controlled ventilation of a patient, especially of a patient with reduced spontaneous breathing. The device comprises a ventilator unit, by which the patient can be supplied with a breathing air flow composed of cyclical ventilation strokes. Further, a control unit is provided, which generates a ventilator unit control signal and transmits same to the ventilator unit, so that a pressure or a volume flow of the breathing air flow is set as a function of the ventilator unit control signal. An EMG signal, which is used at least at times as the basis for the generation of the ventilator unit control signal in the control unit, is generated with an EMG unit as a function of a breath of the patient. This device according to the present invention further comprises an analyzing unit for analyzing the EMG signal, which analyzes at least one EMG signal recorded during an already concluded breath of the patient, especially during the phase of inspiration of the breath. The control unit is configured such that the ventilator unit control signal can be generated, at least at times, by taking into account the analysis of the EMG signal recorded during an already concluded breath of the patient. It is thus essential for the device according to the present invention that the ventilator unit is actuated, at least at times, by taking into account the EMG signal of at least one past breath. Further, in a preferred manner, the ventilator unit is actuated taking into account EMG signals that were recorded during a plurality of past, already concluded breaths and represent the patient's breathing efforts. It is thus possible by means of the technical solution according to the present invention according to a special variant to control the control unit of a pressure-supported or pressure-controlled ventilation of a patient with reduced spontaneous breathing on the basis of currently recorded EMG signals and thus to use the measured values recorded in real time for the actuation of the ventilator unit of the ventilator and to make use of EMG signals, which were recorded during past, already concluded breaths, only in the cases in which no real-time EMG signals are available or the signals lack sufficient signal quality. A device configured according to the present invention offers in this case the advantage that a reliable control signal is generated for the ventilator even in the case in which the EMG signal is at times poor, e.g., due to artifacts or detachment of electrodes, because this is based on the EMG signal of a past, already concluded breath and hence on the patient's past breathing activity.

It is thus essential for the present invention that a control signal, which is based on a breathing activity exerted by the patient in the past, is generated on the basis of EMG signals. It is pointed out in this connection that a corresponding control signal does not necessarily have to be, from a technical point of view, a control signal for the ventilator unit of a ventilator. Rather, a correspondingly generated control signal may also be used, as an alternative or in addition, to actuate other medical devices, e.g., a monitor and/or a device for dispensing drugs.

A special embodiment of the present invention is characterized in that the EMG signal analyzing unit for analyzing an EMG signal is configured such that a quality value of a recorded EMG signal, especially of a currently recorded EMG signal, is determined by the analyzing unit and the determined quality value is compared in a comparison unit with a quality limit value. Taking the analysis of the EMG signal recorded during an already concluded breath of the patient into account, the ventilator unit control signal is preferably generated as soon as the quality value drops below the quality limit value. The essential idea of this special solution is consequently to monitor the quality of the EMG signal recorded during at least one breath in real time and to use an EMG signal of at least one past, concluded breath of the patient for generating a ventilator unit control signal if no current EMG signal is present or if the signal quality of this signal does not appear to be sufficient for generating a ventilator unit control signal from this. The ventilation pressure, the inspiration time and/or a gradient of the pressure or of the volume flow during a breath are, in turn, set by means of the control signal.

The principle of regulation according to the present invention is thus based on the fact that the ventilation pressure applied or the volume flow is determined on the basis of EMG measurements of the past, already concluded breaths, at least provided that the measured values currently being recorded cannot be used to actuate the ventilation. The EMG activity is thus preferably measured during a breath and the pressure support and/or the duration and the slope of the rise of a ventilation stroke is controlled in the next cycle corresponding to at least one previously recorded EMG signal, at least if the current measured values show qualitative defects.

In a special embodiment of the present invention, the analyzing unit for analyzing an EMG signal determines within the framework of the analysis of at least one EMG signal an integral or a time mean value over an enveloping curve of the EMG signal recorded during at least one fully concluded breath of the patient. The analysis of the EMG signal may be carried out, as an alternative or in addition, such that a maximum, a median and/or a standard deviation of the EMG signal recorded during at least one fully concluded breath is taken into account. If EMG signals that were recorded during more than one past breath are used when generating a ventilator unit control signal, the above-mentioned measures may, of course, be taken into account either such that all these breaths or only some of these breath are taken into account.

The unit for analyzing an EMG signal performs an analysis of the EMG signal for a first breath and for at least one second fully concluded breath of the patient. Separate quality values are preferably available in this case for the individual, already concluded breaths that took place in the past.

In a special variant of the present invention, a mean value, especially a weighted mean value is formed, and/or a filtering of the EMG signals recorded currently and/or in the past is performed during the analysis of the at least one EMG signal. EMG signals already recorded in the past are analyzed in this case in an especially advantageous manner and quality values or measured values are set for the different EMG signals that were recorded during different past breaths. The respective EMG signals represent an indicator for the breathing activity of the patient during the respective breath. EMG signals are preferably recorded and analyzed for any desired number of past breaths by cumulating the quality values of the EMG signals recorded during different breaths into a quality value by forming a weighted mean or filtering in order to generate a control signal for actuating the ventilator unit of the ventilator on the basis of this combined quality value.

The setting of the time interval in which the patient takes a breath, i.e., inhales, is an essential feature of the device according to the present invention for generating a ventilator unit control signal on the basis of EMG signals, which were recorded during already concluded, past breaths. A breath is defined in this case as breathing activity of the patient that begins with the inspiration and ends at the end of the inspiration. This time period is also called phase of inspiration, during which the lungs are filled with air. To set the duration of such a breath in a suitable manner, the analysis unit for analyzing an EMG signal sets a start of the breath of the patient preferably at a time at which the EMG signal reaches or exceeds a triggering threshold value stored in the unit. Furthermore, an end point of the breath is advantageously set at a time at which the EMG signal reaches or drops below a cycling-off threshold value, which is likewise stored in the unit.

Based on such a determination of the time at which a breath of the patient being ventilated starts and ends, a time period or duration of the breath or of the phase of inspiration can advantageously be determined on the basis of the previously determined start and end. If EMG signals that were recorded during more than one past breath of the patient shall be taken into account, the durations of the past breaths can be determined and a mean duration can be determined from this for example, by means of forming a weighted mean. This mean duration of a breath can now advantageously be used to determine the quality value and/or the actuation of the ventilator unit for generating a suitable ventilation stroke.

According to a special embodiment of the present invention, an indicator is determined by the analysis unit for analyzing an EMG signal for a gradient of the EMG signal and hence for a change in the breathing effort during a breath. Such a gradient for a change in the breathing effort of a patient during a breath or during the corresponding EMG signal is determined by means of calculating the linear regression or by calculating a differential quotient. If more than one past breath shall again be taken into account for the determination of the gradient in question, the respective measured values are advantageously combined, e.g., by forming a weighted mean. The resulting measured value can then be used to generate a ventilator unit control signal at which the slope of the rise corresponds to the slope of the rise of the EMG signal, determined over at least one past breath, wherein said EMG signal is an indicator of the patient's breathing effort.

Provisions are made in a special embodiment of the present invention for generating the ventilator unit control signal by the control unit on the basis of at least one measured value recorded in the ventilation circuit if the quality value drops below the quality limit value. It is possible according to this embodiment to make use of sensor signals that are obtained within the pneumatic circuit (one or more measured value recorded in the ventilation circuit) for triggering the ventilation stroke and/or for the cycling-off, depending on the EMG signal quality. In this connection the ventilator unit control signals may be generated completely based on sensor signals from the pneumatic circuit (the ventilation circuit) or to take the sensor signals obtained in the pneumatic circuit (the ventilation circuit) at least when generating the ventilator unit control signal, depending on how far the quality value drops below the quality limit value.

In principle, an amplitude of the pressure and/or the volume flow of the breathing air flow fed to the patient may be set by means of a suitably generated ventilator unit control signal as a function of an EMG signal, which was generated during at least one fully concluded breath of the patient. As an alternative or in addition to this, the duration of a ventilation stroke may be set by the control unit in a corresponding manner. In another, very special embodiment of the present invention, the control unit is configured such that a gradient of the pressure and/or of the volume flow, i.e., a corresponding change over time, is varied during the ventilation stroke. It is always significant in this connection that the breathing activity of the patient is taken into account when generating the ventilator unit control signal, and EMG signals that were already recorded during past breaths of the patient are used, at least if the currently recorded EMG signal cannot be used to generate the control signal.

The present invention will be described in more detail below without limitation of the general inventive idea based on exemplary embodiments with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
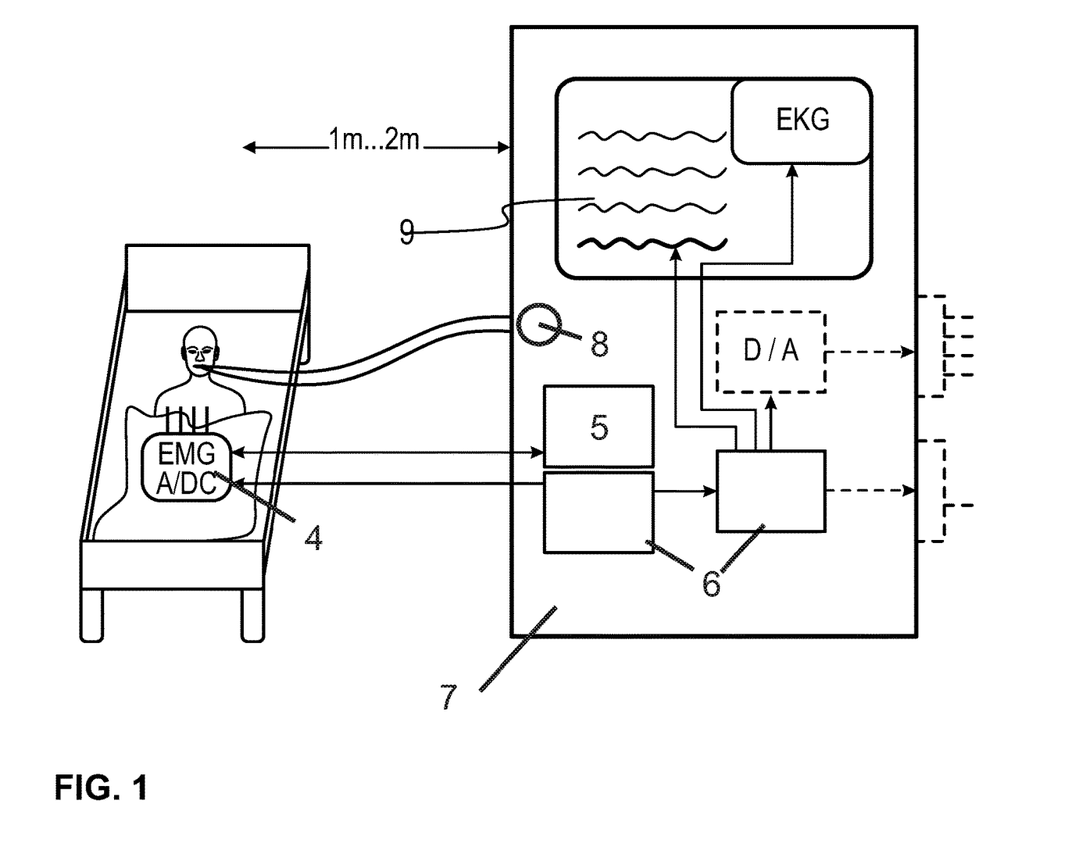
FIG. 1 is a schematic view of the general configuration of a device for the supporting ventilation of a patient with an EIT system and with a control unit supplied by the EIT system with measured signal.

Referring to the drawings, for introduction, the general configuration of a device for the pressure-supported or pressure-controlled ventilation of a patient is shown first in FIG. 1. The device has an EMG system with electrodes 4 for recording EMG signals, which are transmitted to an EMG analysis unit 5. The EMG analysis unit 5 analyzes the received EMG signals, after which ventilator unit control signals, on the basis of which a ventilator unit 8 of the ventilator 7 is actuated as needed, are generated in the control unit 6 of the ventilator 7 on the basis of the analysis of the EMG signals recorded currently and/or at an earlier time. Furthermore, a monitor 9 is provided, on which information on the ventilation parameters set on the ventilator 7 and/or on the state of the patent, especially physiological parameters, are displayed. In particular, information relating to the breathing activity of the patient can be outputted via the monitor 9. In this connection, information relating to the breathing activity of the patient, which information is generated by an analysis of EMG signals, may be outputted via the monitor, without the patient being ventilated by the ventilator 7. Information on the breathing activity of the patient, namely, the patient's spontaneous breathing activity, is outputted in this case via the monitor 9. The control unit 6 is provided in this case, which generates a control signal for actuating the monitor on the basis of the analyzed EMG signals, preferably for at least one already concluded, past breath.

As was shown by the above explanations, there are various possibilities for achieving pressure support, which is based on the essential idea of the present invention. The method described below is the so-called EMG-based "variable pressure support."

The user, usually a physician, sets the ventilator to a pressure target value $P_0$ and optionally sets the pressure limits $P_{max}$ and $P_{min}$. As an alternative, the pressure limits $P_{min}$ and $P_{max}$ may be preset automatically by the control unit of the ventilator as a function of $P_0$, for example, by calculating the values $P_0+/-50\%$.

Furthermore, electrode signals, which represent the patient's breathing activity or breathing effort during a breath, are recorded by means of an electrode belt with electrodes 4 attached in the area of the patient's thorax. These EMG signals are sent to an analyzing unit 5 for analyzing the EMG signals.

The potential fluctuations arising in the area of the thorax are recorded by means of a belt comprising concentric needle electrodes and are transmitted as EMG signals to the EMG analysis unit. The measurements of the potential changes may be with electrodes applied on the skin, by means of surface electrodes, but such surface electrodes are substantially less accurate than needle electrodes.

The analyzing unit 5 for analyzing the EMG signal first determines in real time the time $t_i$ at which the next breath begins as well as the time $t_e$ at which the current breath ends from the current EMG signal 1 and/or from at least one signal (recorded EMG signal), which was recorded in the ventilation circuit. Furthermore, this unit calculates an intensity A from the EMG signal of the last triggered breath. Furthermore, a ventilator unit control signal is generated, on the basis of which a pressure-supported stroke with the pressure value P is generated at the time $t_i$ and is ended at the time $t_e$. The indicator of the pressure support, i.e., the pressure value of the ventilation stroke, is between $P_{min}$ and $P_{max}$. $P=P_0$ is selected initially, while P is subsequently calculated as a function of $P_{min}$ and $P_{max}$, while P is calculated in the further course as a function of $P_0$ and A. A rising intensity A from the EMG signal leads to an increased P and vice versa.

The pressure-supported ventilation of a ventilated patient with reduced spontaneous breathing takes place, as was described above, according to the embodiment described below, which is based on the present invention, but EMG signals 1 from past, already concluded breaths of the patient are additionally taken into account. Taking into account EMG signals from past may include using an immediately preceding breath or corresponding breathing efforts for generating a control signal for the current ventilation stroke.

Figure 2A:
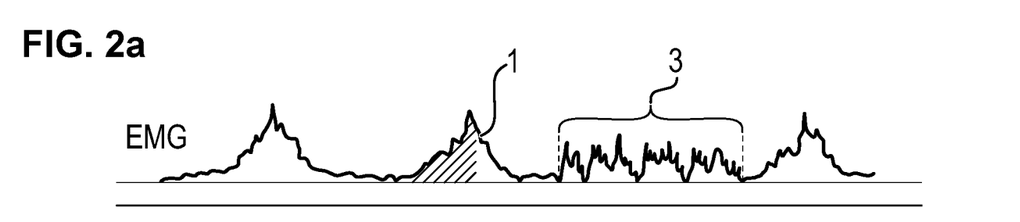
FIG. 2a is an EMG signal diagram with a pressure-supported or pressure-controlled ventilation of a patient with reduced spontaneous breathing, taking EMG signals that were recorded during past breaths into account.
Figure 2B:
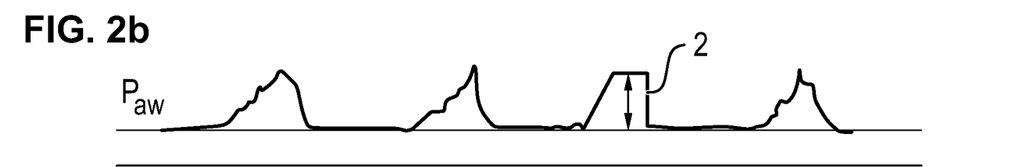
FIG. 2b is a pressure curve signal diagram with a pressure-supported or pressure-controlled ventilation of a patient with reduced spontaneous breathing, taking EMG signals that were recorded during past breaths into account.
Figure 2C:
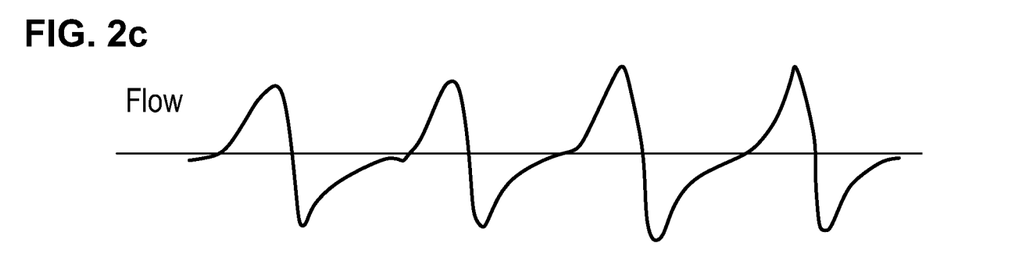
FIG. 2c is a volume flow signal diagram with a pressure-supported or pressure-controlled ventilation of a patient with reduced spontaneous breathing, taking EMG signals that were recorded during past breaths into account.

FIGS. 2a-2c show in this connection the course of an EMG signal 1 (FIG. 2a), the pressure curve 2 during the ventilation (FIG. 2b) and the volume flow during the ventilation (FIG. 2c) in three graphic diagrams. The pressure of the ventilation stroke is generally set based on a ventilator unit control signal such that the airway pressure $P_{AW}$ 2 is proportional to the EMG signal 1. The EMG signal 1, represented in FIG. 2a, shows a disturbance 3, so that no valid EMG signal 1 that could be used as the basis for controlling the ventilator is preset at this time. In particular, no valid EMG signal that would permit a triggering/cycling-off or even proportional ventilation is available. To make it nevertheless possible to continue the ventilation in a meaningful way, the value of the ventilation stroke is determined in this case from the integral of the EMG signal 1 of the preceding breath.

The slope of the ramp or the duration of a ventilation stroke may be determined on the basis of the immediately preceding, already concluded breath or of the EMG signal initiated by this stroke. The method described in connection with FIG. 2 thus ensures that at least the breathing activity, which the patient showed immediately before the onset of the disturbance in the EMG signal, can be taken into account for generating a ventilator unit control signal for the current ventilation stroke.

According to this special embodiment, the unit for analyzing at least one EMG signal additionally determines an indicator for the intensity of the spontaneous breathing efforts of the current breath (Ak), an indicator for the duration of the spontaneous breathing efforts of the current breath (Tk) as well as an indicator for the slope of the rise of the spontaneous breathing efforts of the current breath (Sk). The unit calculates, further, a duration T, an intensity A and a slope of the rise S of the EMG signal from the EMG signal and thus ultimately of the breathing effort represented by this signal. The duration T, the intensity A and the slope of the rise S of the EMG signal are average or mean values, which can be assumed to come at least very close to those that were not recorded during the disturbance 3. The control unit 6 triggers a pressure-supported ventilation stroke with the pressure value P at the time $T_i$ and ends the stroke at the time $T_e$ or after a time depending on the analysis of the EMG signals recorded already before. Further, a ramp is used in the pressure-supported and pressure-controlled ventilation as a function of the slope of the rise S.

Figure 3A:
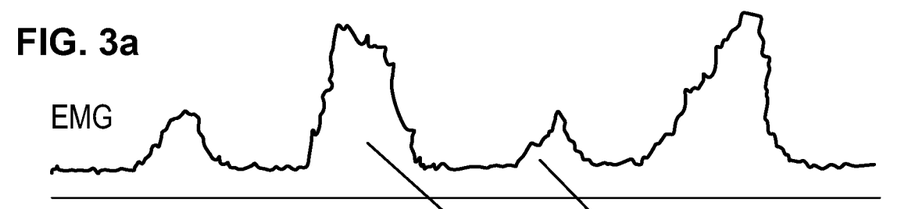
FIG. 3a is an EMG signal diagram of a regulation of the degree of pressure support based on the integral of the EMG signal during the inspiration of the preceding breath.
Figure 3B:
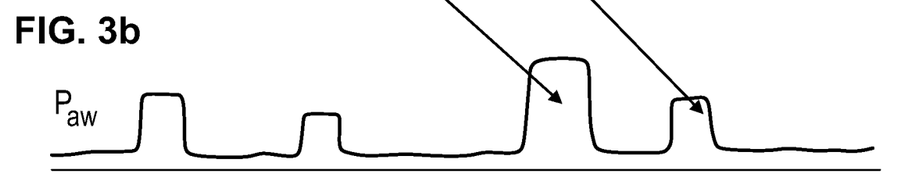
FIG. 3b is an airway pressure signal diagram of a regulation of the degree of pressure support based on the integral of the EMG signal during the inspiration of the preceding breath.
Figure 3C:
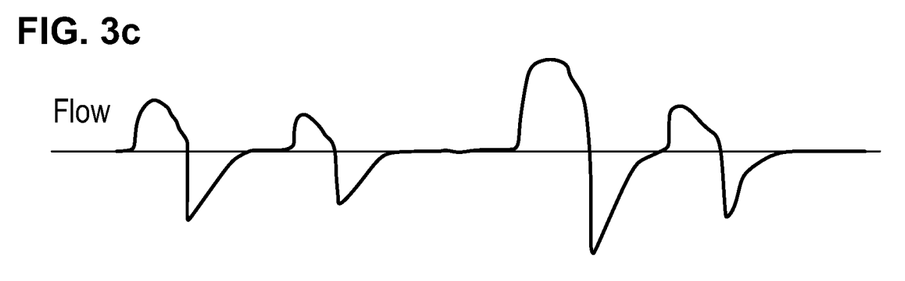
FIG. 3c is a volume flow signal diagram of a regulation of the degree of pressure support based on the integral of the EMG signal during the inspiration of the preceding breath.

FIG. 3a-3c show, further, the regulation of the degree of pressure support based on the integral of the EMG signal during the inspiration of the preceding breath. FIG. 3a shows for this the EMG signal, FIG. 3b the airway pressure $P_{AW}$ and FIG. 3c the volume flow. As can be seen especially in FIGS. 3a and 3b, a control signal is generated for the desired airway pressure $P_{AW}$ during a ventilation stroke on the basis of an integral over the EMG signal 1, which was recorded during a past, already concluded breath. It is essential in this case that if the patient being ventilated shows a high breathing activity, the pressure and/or volume flow provided by the ventilator can correspondingly be reduced. Just as the integral of an EMG signal of a past breath can be used to generate a control signal for the current ventilation stroke, likewise the slope of the rise of the EMG signal, i.e., the derivation of said signal, which reflects a change in the breathing activity of the patient during a breath, may be used to generate a ventilator unit control signal for the current ventilation stroke.

Figure 4A:
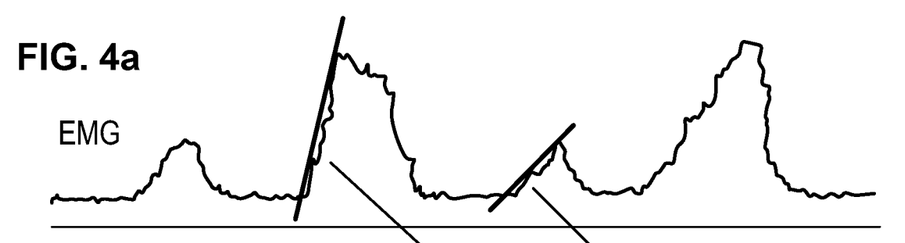
FIG. 4a is an EMG signal view of the regulation of the ramp slope based on the rise of the EMG signal during the inspiration of the preceding breath.
Figure 4B:
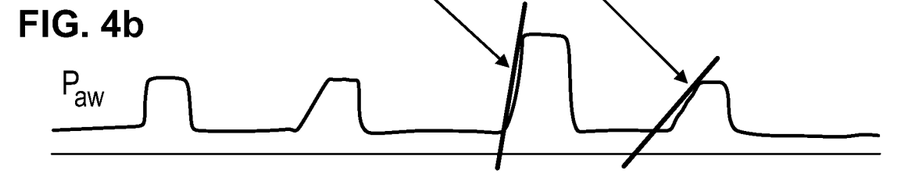
FIG. 4b is an airway pressure signal view of the regulation of the ramp slope based on the rise of the EMG signal during the inspiration of the preceding breath.
Figure 4C:
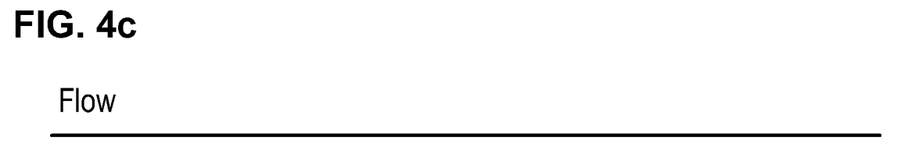
FIG. 4c is a flow signal view of the regulation of the ramp slope based on the rise of the EMG signal during the inspiration of the preceding breath.

Furthermore, FIGS. 4a-4c show, in turn, in a comparison, an EMG signal (FIG. 4a), the airway pressure $P_{AW}$ (FIG. 4b), as well as the volume flow or flow (FIG. 4c). The regulation of the ramp slope, i.e., a pressure change during the ventilation stroke, takes place here as a function of the ramp slope of the breath preceding the current breath or of the EMG signal recorded during the preceding breath.

Thus, an essential idea of the present invention is to perfect a pressure-controlled or pressure-supported ventilation, which is regulated on the basis of EMG signals, such that if an EMG signal is absent or if an EMG signal has an insufficient quality, the EMG signal of at least one preceding, already concluded breath of the patient being ventilated is used to generate suitable control signals. It is, of course, possible, as this was also described here, to use not only an EMG signal that was recorded during a breath immediately preceding the current breath, but also a plurality of past breaths, and to form from this, in a suitable manner, a mean value, median or another indicator, which includes the signals of the preceding breaths and which is used as the basis for generating a control signal.

While specific embodiments of the invention have been shown and described in detail to illustrate the application of the principles of the invention, it will be understood that the invention may be embodied otherwise without departing from such principles.

APPENDIX

List of Reference Numbers

1 EMG signal of a breath
2 Change in the airway pressure during a breath
3 Disturbance in the EMG signal
4 EMG electrodes
5 EMG analysis unit
6 Control unit
7 Ventilator
8 Ventilator unit
9 Monitor

What is claimed is:

1. A device for the pressure-supported or pressure-controlled ventilation of a patient, the device comprising:
a ventilator supplying a patient with a breathing air flow composed of cyclical ventilation strokes, the ventilator selectively varying a pressure or a volume flow or both a pressure and a volume flow of the breathing air flow as a function of a ventilator unit control signal;
an EMG unit configured to generate an electromyography (EMG) signal as a function of a breath of the patient;
an EMG signal analyzing unit configured to analyze a recorded EMG signal and to generate an analysis of the recorded EMG signal, the EMG signal analyzing unit is further configured to determine a quality value for the recorded EMG signal and the quality value is compared with a quality limit value in a comparison unit;
a control unit configured to generate and transmit the ventilator unit control signal to the ventilator, wherein the control unit is configured to generate the ventilator unit control signal for a present breath based on the analysis of the recorded EMG signal of the present breath when the quality value is above the quality limit value, wherein the control unit is further configured to generate the ventilator unit control signal for the present breath based on the analysis of the recorded EMG signal of a past fully concluded breath when the quality value drops below the quality limit value.

2. A device in accordance with claim 1, wherein the analysis of the recorded EMG signal, by the EMG signal analyzing unit, comprises determining an integral or a time mean value over an enveloping curve of the recorded EMG signal of the past fully concluded breath of the patient.

3. A device in accordance with claim 1, wherein the analysis of the recorded EMG signal, by the EMG signal analyzing unit, comprises determining a maximum of the recorded EMG signal or determining a median of the recorded EMG signal, or determining a standard deviation of the recorded EMG signal, or determining any combination of a maximum of the recorded EMG signal, a median of the recorded EMG signal and a standard deviation of the recorded EMG signal, of the past fully concluded breath of the patient.

4. A device in accordance with claim 1, wherein the analysis of the recorded EMG signal, by the EMG signal analyzing unit, comprises forming a mean value of the recorded EMG signal, or forming a weighted mean of the recorded EMG signal, or filtering of the recorded EMG signal or any combination of forming a mean value of the recorded EMG signal, or forming a weighted mean of the recorded EMG signal, or filtering of the of the recorded EMG signal.

5. A device in accordance with claim 1, wherein the EMG signal analyzing unit determines a time for the start of the breath of the patient as a function of the EMG signal reaching or exceeding a triggering threshold value.

6. A device in accordance with claim 1, wherein the EMG signal analyzing unit determines a time for an end of breath of the patient as a function of the EMG signal reaching or dropping below a cycling-off threshold value.

7. A device in accordance with claim 6, wherein the EMG signal analyzing unit for analyzing an EMG signal determines a time period of breath of the patient from a start and an end of the breath.

8. A device in accordance with claim 1, wherein:
the ventilator comprises a ventilation circuit; and
the ventilator unit control signal is generated on the basis of at least one measured value recorded in the ventilation circuit as soon as the quality value drops below the quality limit value.

9. A device in accordance with claim 1, wherein the control unit is configured such that the ventilator unit control signal varies an amplitude of the pressure or an amplitude of the volume flow or an amplitude of the pressure and an amplitude of the volume flow, of the breathing air flow of the ventilator.

10. A device in accordance with claim 1, wherein the control unit is configured such that the ventilator unit control signal changes a gradient of the pressure or a gradient of the volume flow or a gradient of the pressure and a gradient of the volume flow, during the ventilation stroke of the ventilator.

11. A control signal device for generating a control signal for at least one medical device, the control signal device comprising:
an EMG unit generating an electromyography (EMG) signal;
a control unit configured to transmit the control signal via a data path to the at least one medical device and to exchange data at least at times with the EMG unit or to transmit the control signal to the EMG unit or to transmit the control signal via a data path to the at least one medical device and to exchange data at least at times with the EMG unit and to transmit the control signal to the EMG unit, wherein the EMG signal is used at least at times as a basis for generating the control signal in the control unit, as a function of a breath of the patient; and an analyzing unit for analyzing a recorded EMG signal, the analyzing unit configured to determine a quality value for the recorded EMG signal and further configured to compare the quality value with a quality limit value in a comparison unit;

wherein the control unit is configured to generate the control signal for a present breath based on the analysis of the recorded EMG signal of the present breath when the quality value is above the quality limit value, wherein the control unit is further configured to generate the control signal for the present breath based on the analysis of the recorded EMG signal of a past fully concluded breath when the quality value drops below the quality limit value.

12. A device in accordance with claim 11, wherein the at least one medical device is a monitor, via which at least one piece of information, relating to a breathing activity of the patient, is outputted.

13. A device for ventilating a patient, the device comprising:
  a ventilator configured to supply a patient with cyclical ventilation strokes, the ventilator selectively varying, the cyclical ventilation strokes as a function of a ventilator control signal;
  an EMG unit configured to measure an electromyography (EMG) signal of the patient over a plurality of breaths of the patient during ventilation of the patient;
  a ventilator control unit configured to generate the ventilator control signal and to transmit the ventilator control signal to said ventilator, said ventilator control unit is configured to selectively generate the ventilator control signal between being based on either the EMG signal of a present breath or a past fully concluded breath, wherein the selective generation of the ventilator control signal is based on a quality value.

14. A device in accordance with claim 13, wherein:
  an EMG signal analyzing unit is provided and is configured to analyze the EMG signal, said EMG signal analyzing unit configured to determine the quality value for the EMG signal of the present breath;
  said ventilator control unit generates the ventilator control signal based on the past fully concluded breath when the quality value is below a quality limit value.

* * * * *